United States Patent

Broggi et al.

[11] 3,998,950
[45] Dec. 21, 1976

[54] 7-αHYDRAZINOACETAMIDO DERIVATIVES OF CEPHALOSPORANIC ACID

[75] Inventors: Renato Broggi, Milan; Giuseppe Libassi, Gruppello-Gavirate (Varese); Giorgio Pifferi, Milan, all of Italy

[73] Assignee: ISF S.p.A., Milan, Italy

[22] Filed: Mar. 28, 1975

[21] Appl. No.: 563,135

[30] Foreign Application Priority Data
Apr. 2, 1974   Italy .................................. 49985/74

[52] U.S. Cl. ........................... 424/246; 260/243 C; 260/468 J
[51] Int. Cl.² ............ A61K 31/545; C07D 501/22; C07D 501/32; C07D 501/34; C07D 501/42
[58] Field of Search .............. 260/243 CN; 424/246

[56] References Cited
UNITED STATES PATENTS
3,489,752   1/1970   Crast ............................. 260/243 C
3,518,260   6/1970   Spencer et al. ................ 260/243 C OTHER PUBLICATIONS
Takano, "Chemical Abstracts," 1972, vol. 76, p. 420, abstract 153,762u.

*Primary Examiner*—Nicholas S. Rizzo
*Assistant Examiner*—David E. Wheeler
*Attorney, Agent, or Firm*—Stevens, Davis, Miller & Mosher

[57] ABSTRACT

Derivatives of 7-aminocephalosporanic acid of the formula:

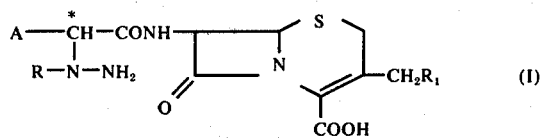

wherein the carbon atom marked with an asterisk represents an asymmetry center of the molecule, A represents an aromatic nucleus, preferably phenyl which may be substituted by alkyl having 1–4 carbon atoms, halogen, hydroxy or alkoxy having 1–4 carbon atoms, or a heterocyclic nucleus, preferably 2- or 3-thiophene which may be, for example, substituted by halogen, R represents a hydrogen atom or a straight or branched chain lower alkyl radical, $R_1$ represents a hydrogen atom, a hydroxy group, an acetoxy or pyridinium group. The invention includes the compounds as such or in the form of separated epimers as well as the corresponding pharmaceutically acceptable salts with alkali or alkaline-earth metals, with suitable organic bases or corresponding suitable organic or inorganic acid addition salts. Also method of preparing same. The compounds have powerful antibacterial action against gram-positive and gram-negative bacteria.

19 Claims, No Drawings

7-αHYDRAZINOACETAMIDO DERIVATIVES OF CEPHALOSPORANIC ACID

The present invention relates to biologically active derivatives of aminocephalosporanic acid and a process for the preparation thereof.

The new derivatives of 7-aminocephalosporanic acid of the invention have the general formula:

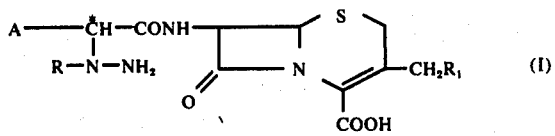

wherein the carbon atom marked with an asterix represents an asymmetry center of the molecule, A represents an aromatic nucleus, preferably phenyl which may be substituted by alkyl having 1-4 carbon atoms, halogen, hydroxy or alkoxy having 1-4 carbon atoms, or a heterocyclic nucleus, preferably 2-or 3-thiophene which may be, for example, substituted by halogen, R represents a hydrogen atom or a straight or branched chain lower alkyl radical, $R_1$ represents a hydrogen atom, a hydroxy group, an acetoxy or pyridinium group. The invention includes the compounds as such or in the form of separated epimers as well as the corresponding pharmaceutically acceptable salts with alkali or alkaline-earth metals, with suitable organic bases or corresponding suitable organic or inorganic acid addition salts.

Preferably, salts with alkali or alkaline-earth metals are sodium and potassium salts, preferred organic bases are amines such as triethylamine, procaine, dibenzylamine and N,N-dibenzylethylenediamine and the preferred acids are, among the inorganic ones, hydrochloric acid, hydrobromic hydriodic, sulphuric and phosphoric acids and, among the organic ones, acetic, succinic, maleic, citric, benzoic, tartaric and ascorbic acids.

The process according to the present invention, for the preparation of compounds of formula (I) comprises reacting 7-aminocephalosporanic acid (II) in protected form with a derivative of α-hydrazinacetic acid of formula (III)

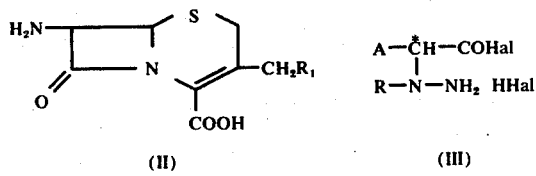

wherein $R_1$, the carbon atom marked with the asterisk, A and R have the above meaning and Hal represents a chlorine or bromine atom, in an anhydrous aprotic solvent, in the presence of an acceptor of hydrohalic acid and in subsequently removing the protecting group of 7-aminocephalosporanic acid. Synthesis runs rapidly and takes place between the reactants dissolved in a solvent such as, for example, acetonitrile, methylene chloride or chloroform, preferably at a temperature comprised between −40° C and 30° C. Weak tertiary bases among which are preferred dimethylaniline and quinoline or propylene oxide, can be used as the acceptor of the hydrohalic acid which forms during condensation. In order to protect, during the synthesis, the free carboxylic group in position 4 of the cephalosporanic nucleus, the same is, in the usual way, converted into the corresponding salt, for example into sodium or potassium salt, which is subsequently converted, once condensation is complete, into the free acid; or, preferably, the carboxylic group is protected using a suitable sililating agent such as, for example, hexamethyldisilazane, trimethylchlorosilane, triethylbromosilane, and tri-n-butylchlorosilane which, once condensation is complete, is then removed to restore the free carboxylic group.

Alternatively, the carboxylic group of the cephalosporanic nucleus can be protected with β,β,β-trichloroethyl radical; the products obtained by condensation between the hydrogen halide of the α-hydrazinacetic acid derivative (III) and trichloroethylester of cephalosporanic acid or of a derivative thereof (II) form a new, interesting class of compounds of the formula:

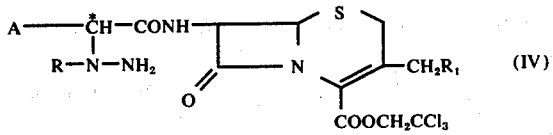

wherein the carbon atom marked with the asterisk represents a center of asymmetry of the molecule and A, R and $R_1$ have the above meanings with the exception of $R_1$ being hydroxy, from which it is possible, by removing the protecting trichloroethyl group by suitable means, to obtain the compounds of formula (I). Compounds (IV) wherein $R_1$ is hydroxy, are obtained from the corresponding 3-acetoxy by hydrolysis.

The preparation of the corresponding epimers of the compounds of the invention is carried out starting from optically active forms of α-hydrazino or α-alkylhydrazino substituted acetic acid, subsequently converted into the optically active forms of the corresponding hydrogen halides of formula (III) from which, in accordance with the process of the invention, forms R(−) and S(+) of the compounds of formula (I) are obtained. The terms "alkyl" and "lower alkyl" mean alkyl radicals containing from 1 to 5 carbon atoms. The compounds of the present invention show an interesting activity as wide-spectrum antibacterial agents and are active on resistant germs; they are usefully used as such or combined with pharmaceutically acceptable carriers. The following examples, which are in no way limitative, serve to illustrate the invention.

EXAMPLE I 7-(α-Hydrazinophenylacetamido)-desacetoxycephalosporanic acid

To a suspension of 2.14 g 7-aminodesacetoxycephalosporanic acid in 20 ml acetonitrile and 20 ml methylene chloride, 2.5 ml hexamethyldisilazane are added. The mixture is refluxed for 90 minutes, then cooled and evaporated to dryness under vacuo a room temperature. The residue is dissolved in 30 ml acetonitrile and 20 ml propylene oxide, cooled to −20° C and mixed with stirring with 2.6 g of chloride of α-hydrazinophenylacetic acid hydrochloride. Cooling is interrupted and the solution allowed to react at room temperature for 2 hours. The precipitate is filtered under vacuum, washed with acetonitrile and dried under vacuum over phosphoric anhydride at room temperature. 2.35 grams of 7-(α-hydrazinophenylacetamido)-desacetoxycephalosporanic acid are obtained which, purified by chromatography, melts at 168°–172° C (with decomposition); $[\alpha]_D^{25°C}$ 32 + 125° (C = 0.05, buffer pH 4.4).

EXAMPLE II

7-(R(−)-α-hydrazinophenylacetamido-desacetoxycephalosporanic acid

The procedure is as described in Example I starting from 1.25 ml hexamethyldisilazane, 1.07 g 7-aminodesacetoxycephalosporanic acid and 1.3 g of chloride of R(−) - α-hydrazinophenylacetic acid hydrochloride; 1.45 g 7-(R(−)- α-hydrazinophenylacetamido)-desacetoxycephalosporanic acid are obtained melting at 158°–160° C (with decomposition). $[\alpha]_D^{25°C} = +183°$ (C = 0.05, buffer 4.4).

EXAMPLE III

7-(S(+)-α-hydrazinophenylacetamido)-desacetoxycephalosporanic acid

The procedure is as described in Example I, starting from 0.97 ml hexamethyldisilazane, 0.83 g 7-aminodesacetoxycephalosporanic acid and from 1 g chloride of S(+) - α-hydrazinophenylacetic acid hydrochloric; 1.2 g 7-(S(+)- α-hydrazinophenylacetamido)-desacetoxycephalosporanic acid are obtained melting at 160°–162° C (with decomposition), $[\alpha]_D^{25°C} = +165°$ (C = 0.05, buffer 4.4).

EXAMPLE IV

7-(α-hydrazinophenylacetamido)-cephalosporanic acid

To a suspension of 0.9 g 7-aminocephalosporanic acid in 7 ml acetonitrile and 7 ml methylene chlorie, 0.83 ml hexamethyldisilazane are added, heating at 50° C for 1 hour. The solution is cooled and evaporated to dryness under vacuum and at room temperature. The residue is dissolved in 10 ml acetonitrile and 7 ml propylene oxide, cooled to −20° C and 0.86 g chloride of α-hydrazinophenylacetic acid hydrochloride are added under stirring. Cooling is stopped and the mixture allowed to react at room temperature for two hours. The precipitate is filtered under vacuum, washed with acetonitrile and dried over phosphoric anhydride under vacuum and at room temperature. There are obtained 1.4 gram of 7-(α-hydrazinophenylacetamido)-cephalosporanic acid which, after purification by chromatography, melts at 218°–220° C (with decomposition). $[\alpha]_D^{25°C} = +75°$ (C = 1, acetonitrile/water, 1 : 1).

EXAMPLE V

7-(R(−)-α-hydrazinophenylacetamido)-cephalosporanic acid

The procedure is as described in Example IV starting from 0.83 ml hexamethyldisilazane, 0.9 g 7-aminocephalosporanic acid and from 0.87 g chloride of R(−)- α-hydrazinophenylacetic acid hydrochloride; 1.25 g 7-(R(−) α-hydrazinophenylacetamido)-cephalosporanic acid are obtained melting at 220°–222° C (with decomposition). $[\alpha]_D^{25°C} = +48°$ (C = 1, acetonitrile/water, 1:1).

EXAMPLE VI

7-(S(+)- α-hydrazinophenylacetamido cephalosporanic acid

The procedure is as described in Example IV starting from 0.83 ml hexamethyldisilazane, 0.9 g 7-aminocephalosporanic acid and from 0.86 g chloride of S(+)- α-hydrazinophenylacetic acid hydrochloride; 1.25 g 7-S(+)- α-hydrazinophenylacetamidocephalosporanic acid are obtained melting at 220°–222° C (with decomposition). $[\alpha]_D^{25°C} = +114°$ C (C = 1, acetonitrile/water, 1:1).

EXAMPLE VII

7-[α-(1-methylhydrazino)phenylacetamido]desacetoxycephalosporanic acid

To a suspension of 1.4 g of 7-aminodesacetoxycephalosporanic acid in 10 ml acetonitrile and 10 ml methylene chloride, 1.64 ml hexamethyldisilazane are added and the resulting mixture is refluxed for 90 minutes. The solution is cooled and evaporated to dryness under vacuum at room temperature. The residue is dissolved at 5° C in 20 ml acetonitrile and 13 ml propylene oxide; the solution is cooled to −25° C and mixed stirring with 2.1 g chloride of α - (1-methylhydrazino) phenylacetic acid hydrochloride. THe solution is allowed to react for 3 hours at 0° C and filtered under vacuum; from the filtration mother liquors, by treatment with ether, 1.15 g 7-[α-(1-methylhydrazino)phenylacetamido] desacetoxycephalosporanic acid melting at 185°–190° C (with decomposition) are obtained. $[\alpha]_D^{25°C} = +116.2$ (C = 0.1, buffer pH 4.4).

EXAMPLE VIII

7-(α-hydrazinophenylacetamido)-desacetoxycephalosporanic acid

7-(α-hydrazinophenylacetamido)-desacetoxycephalosporanic acid β- β- β-trichloroethylester To a solution of 8.7 g 7-aminodesacetoxycephalosporanic acid β- β- β-trichloroethylester in 35 ml methylene chloride, 5.95 g chloride of α-hydrazinophenylacetic acid hydrochloride are added. The resulting mixture is cooled to −20° C and 2.5 ml propylene oxide dissolved in 7 ml methylene chloride are added dropwise. The temperature is slowly raised to 25° C over a period of half an hour, then stirring is continued at such temperature for 3 hours. The solvent is removed under vacuum until dryness and the residue is taken with isopropyl ether. The product is collected by filtration, dissolved in methylene chloride and treated with a saturated solution of sodium bicarbonate, separating the organic layer. After washing with water and making the solution anhydrous, the solvent is evapoated and 12.7 g 7-(α-hydrazinophenylacetamido) desacetoxycephalosporanic acid β, β, β-trichloromethylester are obtained which, after purification by precipitation, melts at 160° C (with a first decomposition at 124° C). $[\alpha]_D^{25°C} = +26.6°$ (C = 1, chloroform).

A solution of 10.7 g 7-(α-hydrazinophenylacetamido)-desacetoxycephalosporanic acid β, β, β-trichloroethylester in 22 ml 90% formic acid is added to a suspension of 5.2 g of zinc powder in 6 ml of 90% formic acid at 0° C. After two hours and a half the mixture is filtered and the limpid solution evaporated under vacuum at room temperature. The residue is dissolved in 5 ml water and 5 ml formic acid, treated with triethylamine until pH 3.5, diluted with 200 ml acetonitrile and allowed to crystallize while cold. The zinc salt of cephalosporin is collected by filtration and melts at 218°–219°C (with decomposition). $[\alpha]_D^{25°C} = +109°$ (C = 0.05, buffer pH 4.4).

7-(α-hydrazinophenylacetamido)-desacetoxycephalosporanic acid having the characteristics of the compound in Example I is obtained by recovery from the corresponding zinc salt.

Operating in a similar manner, using the separated active forms R(−), S(+) of chloride of α-hydrazinophenylacetic acid there are first obtained:

-7-[R(−)-α-hydrazinophenylacetamido]-desacetoxycephalosporanic acid β,β,β-trichloroester -7-[S(+)-α-hydrazinophenylacetamido]-desacetoxycephalosporanic acid β,β,β-trichloroethylester respectively and then the corresponding 7-[R(−)-α-hydrazinophenylacetamido]-desacetoxycephalosporanic acid and 7-(S(+)-α-hydrazinophenylacetamido)-desacetoxycephalosporanic acid.

EXAMPLE IX

7-(α-Hydrazino-2-thienylacetamido)desacetoxycephalosporanic acid

To a suspension of 2.14 g 7-aminodesacetoxycephalosporanic acid in 20 ml methylene chloride are added 2.08 ml hexamethyldisilazane and the mixture is refluxed. After one hour 20 ml acetonitrile are added and the mixture further refluxed for an additional hour. The solution is cooled and evaporated to dryness under vacuum at room temperature. The residue is dissolved in 30 ml methylene chloride, cooled to −20° C and mixed with stirring with 3.2 ml N,N-dimethylaniline and portionwise with 4.54 g chloride of α-hydrazino-2-thienyl-acetic acid hydrochloride. The temperature is gradually raised to 10° C over a period of 105 minutes; the solution is cooled to 0° C, 10 ml water are added, the layers are separated and the aqueous layer adjusted to pH 5 with triethylamine. The precipitate is filtered and 150 ml isopropanol are added to the filtrate, cooled to 0° C. The mixture is stirred for 5 minutes and the precipitate filtered under vacuum, washing abundantly with isopropanol and diethyl ether. The compound is dried under vacuum over phosphoric anhydride at room temperature and 1.49 g 7-(α-hydrazino-2-thienylacetamido)-desacetoxycephalosporanic acid melting at 182°–183° C are obtained. $[\alpha]_D^{25°C} = +92°$ (C = 0.05, buffer pH 4.4).

EXAMPLE X

7-(α-Hydrazino-2-thienylacetamido)-cephalosporanic acid

The procedure is as described above using as starting materials 2.72 g of 7-aminocephalosporanic acid; 1.79 g 7-(α-hydrazino-2-thienylacetamido)-cephalosporanic acid are obtained melting at 214°–216° C (with decomposition) $[\alpha]_d^{25°C} = +69.5°$ (C = 1, acetonetrile/water 1:1).

EXAMPLE XI

7-(α-Hydrazino-3-thienylacetamido)-desacetoxycephalosporanic acid

The procedure is as above described using as the starting material 1.07 g 7-aminodesacetoxycephalosporanic acid and α-hydrazino-3-thienyl-acetyl chloride hydrochloride. There are obtained 1.09 g 7-(α-hydrazino-3-thienylacetamido)-desacetoxycephalosporanic acid melting at 172°–174° C $[\alpha]_D^{25°C} = +79.5°$ (C = 0.05, buffer pH 4.4).

EXAMPLE XII

7-(α-Hydrazino-3-thienylacetamido)-cephalosporanic acid

The procedure is as described above using as the starting material 1.36 g of 7-aminocephalosporanic acid and α-hydrazino-3-thienylacetyl chloride hydrochloride. There is obtained 1 g of 7-(α-hydrazino-3-thienylacetamido)-cephalosporanic acid melting at 174°–176° C (with decomposition). $[\alpha]_D^{25°C} = +64°$ (C = 1, acetonitrile/water 1:1).

EXAMPLE XIII

7-(α-Hydrazino-3-(2,5)dichloro)-thienylacetamidocephalosporanic acid 1.04 milliliters of hexamethyldisilazane are added to a suspension of 1.36 g 7-aminocephalosporanic acid in 10 ml methylene chloride and 10 ml acetonitrile. The resulting mixture is heated to 45° C for 1 hour, cooled and dried under vacuum at room temperature. The residue is dissolved in 15 ml methylene chloride and 10 ml propylene oxide. The mixture is cooled to −20° C and 1.77 g chloride of 2,5-dichloro-α-hydrazino-3-thienylacetic acid hydrochloride are added portionwise. The reaction is allowed to proceed at −20° C for 30 minutes, then the temperature is spontaneously left to raise up to +22° C. 30 milliliters of petroleum ether are added, the raw product filtered and subsequently dissolved in H₂O-tetrahydrofuran. The pH is adjusted to 4.8 and isopropanol is added to complete precipitation. From the product, filtered and washed with ether, 2.02 g of 7-[α-hydrazino-3-(2,5-dichloro)-thienylacetamido]cephalosporanic acid melting at 180°–182° C (with decomposition) are obtained. $[\alpha]_D^{25°C} = +65°$ (C = a, acetone/water 2:1).

EXAMPLE XIV

7-[α-hydrazino-3-(2,5-dichloro)thienylacetamido]-desacetoxycephalosporanic acid The procedure is as described above starting from 1.07 g of 7-aminodesacetoxycephalosporanic acid. 1.81 g of 7-[α-hydrazino-3-(2,5-dichloro)-thienylacetamido]desacetoxycephalosporanic acid melting at 208°–210° C (with decomposition) are obtained. $[\alpha]_D^{25°C} = +65°$ (C = 0.05, acetone/water 2:1).

The new cephalosporins according to the invention are useful in chemotherapy, these compounds being endowed with powerful antibacterial action against gram-positive and gram-negative bacteria and with a high degree of resistance both to acids and penicillinase. In fact the compounds of the invention do not lose their biological activity even when contacted for a period of one hour with N/20 HCl or with penicillinase. The Minimum Inhibiting Concentrations (MIC) in vitro of the new cephalosporins expressed in γ/ml were evaluated on some pathogenic microorganisms in comparison to a commercially known wide-spectrum cephalosporin, 7 β-(D-2-aminophenylacetamido)-3-methylceph-3-em-4-carboxilic acid, or cephalexin. Minimum inhibiting concentration (MIC) is a well-known standard and the comparative tests were conducted according to the method of D. C. Grove and W. A. Randall as described in Med. Enc. N.Y., page 190 (1955). The data obtained are listed in the following tables. The cephalosporins of the present invention are utilized in the same manner as in cephalexin.

| MICROORGANISMS | 7-(alpha-hy-drazinophenyl-acetamido)-desacetoxyce-phalosporanic acid | 7-(R(−))alpha hydrazinophen-ylacetamido)-desacetoxyce-phalosporanic acid | 7-(S-(+)alpha hydrazinophen-ylacetamido)-desacetoxyce-phalosporanic acid | 7-(alpha-hy-drazinophenyl-acetamido)-ce-phalosporanic acid | 7-(R(−)-alpha-hydrazinophen-ylacetamido)-cephalospora-nic acid | 7-(S(+)-alpha-hydrazinophen-ylacetamido)-cephalospora-nic acid |
|---|---|---|---|---|---|---|
| Staphylococcus aureus penicil. sensitive | 0.39 | 0.78 | 0.78 | 0.78 | 0.39 | 0.78 |
| Staphylococcus aureus penicil. resistant | 1.56 | 1.56 | 1.56 | 1.56 | 0.78 | 3.12 |
| Streptococcus pyogenes beta-haemoliticus | 0.19 | 0.19 | 0.39 | 0.19 | 0.19 | 0.19 |
| Streptococcus pyogenes | 0.39 | 0.39 | 0.78 | 0.39 | 0.19 | 0.39 |
| Diplococcus pneumoniae | 0.78 | 0.78 | 0.78 | 0.78 | 0.78 | 1.56 |
| Streptococcus faecalis | 50 | 50 | 50 | 50 | 50 | 50 |
| Bacillus subtilis | 0.19 | 0.19 | 0.39 | 0.39 | 0.19 | 0.19 |
| Sarcina lutea | 0.047 | 0.047 | 0.095 | 0.095 | 0.047 | 0.095 |
| Escherichia coli | 3.12 | 6.25 | 3.12 | 3.12 | 3.12 | 6.25 |
| Escherichia coli (beta-lactamasi producer) | 6.25 | 6.25 | 6.25 | 6.25 | 3.12 | 6.25 |
| Shigella sonnei | 1.56 | 1.56 | 1.56 | 1.56 | 0.78 | 1.56 |
| Shigella dysenteriae | 1.56 | 1.56 | 1.56 | 1.56 | 0.78 | 1.56 |
| Salmonella typhimurium 1 | 3.12 | 3.12 | 3.12 | 3.12 | 1.56 | 3.12 |
| Salmonella typhimurium 2 | 3.12 | 3.12 | 3.12 | 3.12 | 1.56 | 3.12 |
| Salmonella paratyphy | 1.56 | 1.56 | 1.56 | 3.12 | 1.56 | 3.12 |
| Pseudomonas aeruginosa | 50 | 50 | 50 | 50 | 50 | 50 |
| Klebsiella pneumoniae | 3.12 | 3.12 | 6.25 | 3.12 | 1.56 | 6.25 |
| Proteus vulgaris | 50 | 50 | 50 | 50 | 50 | 50 |
| Proteus mirabilis | 12.5 | 12.5 | 12.5 | 12.5 | 6.25 | 12.5 |

| MICROORGANISMS | 7-[alpha-(1-methylhydra-zino)-1-phen-ylacetamido]-desacetoxyce-phalosporanic acid | 7-(alpha-hy-drazino-2-thienylaceta-mido)-desaceto-xycephalospo-ranic acid | 7-(alpha-hy-drazino-2-thienylaceta-mido)-cephalo-sporanic acid | 7-(2,5-dichloro-alpha-hydrazino-3-thienylaceta-mido)-cephalospo-ranic acid | 7-(alpha-hy-drazino-3-thienylaceta-mido)-cephalo-sporanic acid | cefalexin |
|---|---|---|---|---|---|---|
| Staphylococcus aureus penicil. sensitive | 0.39 | 0.78 | 0.39 | 0.39 | 0.39 | 0.78 |
| Staphylococcus aureus penicil. resistant | 1.56 | 1.56 | 0.39 | 0.78 | 0.78 | 3.12 |
| Streptococcus pyogenes beta-haemoliticus | 0.39 | 0.39 | 0.095 | 0.19 | 0.39 | 0.39 |
| Streptococcus pyogenes | 0.39 | 0.78 | 0.19 | 0.19 | 0.39 | 0.78 |
| Diplococcus pneumoniae | 0.78 | 0.78 | 0.78 | 0.19 | 0.39 | 1.56 |
| Streptococcus faecalis | 50 | 50 | 50 | 50 | 50 | 100 |
| Bacillus subtilis | 0.19 | 0.39 | 0.095 | 0.19 | 0.19 | 0.39 |
| Sarcina lutea | 0.047 | 0.047 | 0.047 | 0.047 | 0.047 | 0.095 |
| Escherichia coli | 6.25 | 3.12 | 1.56 | 3.12 | 3.12 | 12.5 |
| Escherichia coli (beta-lactamasi producer) | 3.12 | 6.25 | 3.12 | 6.25 | 6.25 | 12.5 |
| Shigella sonnei | 1.56 | 1.56 | 0.78 | 1.56 | 0.78 | 3.12 |
| Shigella dysenteriae | 1.56 | 1.56 | 0.78 | 3.12 | 1.56 | 3.12 |
| Salmonella typhimurium 1 | 3.12 | 3.12 | 1.56 | 3.12 | 1.56 | 6.25 |
| Salmonella typhimurium 2 | 3.12 | 3.12 | 1.56 | 3.12 | 1.56 | 6.25 |
| Salmonella paratyphy | 3.12 | 1.56 | 0.78 | 3.12 | 1.56 | 3.12 |
| Pseudomonas aeruginosa | 50 | 50 | 50 | 50 | 50 | 100 |
| Klebsiella pneumoniae | 6.25 | 3.12 | 1.56 | 3.12 | 3.12 | 6.25 |
| Proteus vulgaris | 50 | 50 | 50 | 50 | 50 | 100 |
| Proteus mirabilis | 12.5 | 12.5 | 3.12 | 6.25 | 3.12 | 25 |

What is claimed is:

1. Hydrazinocephalosporins of the formula:

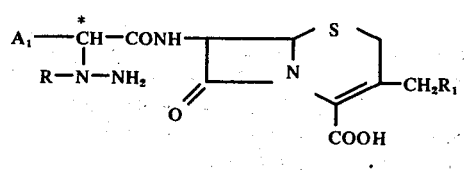

wherein the carbon atom marked with the asterisk represents an asymmetry center of the molecule, $A_1$ represents a phenyl group which may be substituted by alkyl having 1–4 carbon atoms, halogen, hydroxy or alkoxy having 1–4 carbon atoms or a 2- or 3-thiophene group, which may be substituted by halogen, R represents a hydrogen atom or a straight or branched chain lower alkyl radical containing from 1 to 5 carbon atoms, $R_1$ represents a hydrogen atom, a hydroxy, acetoxy or pyridinium group; separated epimers thereof or the corresponding pharmaceutically acceptable salts thereof.

2. 7-(α-Hydrazinophenylacetamido)-desacetoxycephalosporanic acid.

3. 7-[R(−)- α-Hydrazinophenylacetamido]-desacetoxycephalosporanic acid.

4. 7-[S(+)- α-Hydrazinophenylacetamido]-desacetoxycephalosporanic acid.

5. 7-(α-Hydrazinophenylacetamido)-cephalosporanic acid.

6. 7-[R(−)-Hydrazinophenylacetamido]-cephalosporanic acid.

7. 7-[S(+)- α-Hydrazinophenylacetamido]-cephalosporanic acid.

8. 7-[α- (1-Methylhydrazino)phenylacetamido]-desacetoxycephalosporanic acid.

9. 7-(α-Hydrazino-2-thienylacetamido)-desacetoxycephalosporanic acid.

10. 7-(α-Hydrazino-2-thienylacetamido)-cephalosporanic acid.

11. 7-(α-Hydrazino-3-thienylacetamido)-desacetoxycephalosporanic acid.

12. 7-(α-Hydrazino-3-thienylacetamido)-cephalosporanic acid.

13. 7-[α-Hydrazino-3-(2,5-dichloro)-thienylacetamido]-cephalosporanic acid.

14. 7 -[α-Hydrazino-3-(2,5-dichloro)thienylactamido]-desacetoxycephalosporanic acid.

15. Trichloroethylesters of hydrazinocephalosporanic acid of the formula:

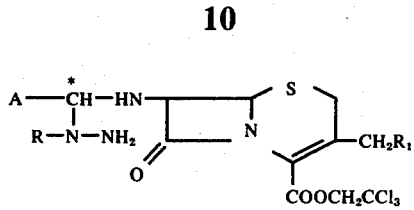

wherein the carbon atom marked with the asterisk represents an asymmetry center of the molecule, A represents a phenyl group which may be substituted by alkyl having 1–4 carbon atoms, halogen, hydroxy or alkoxy having 1–4 carbon atoms or a 2- or 3-thiophene group, which may be substituted by halogen, R represents a hydrogen atom or a straight or branched chain lower alkyl radical, $R_1$ represents a hydrogen atom, a hydroxy, acetoxy or pyridinium group or; separated epimers thereof.

16. 7-(α-Hydrazinophenylacetamido)-desacetoxycephalosporanic acid β, β, β-trichloroethylester.

17. 7-[R(−)-α-Hydrazinophenylacetamido]-desacetoxycephalosporanic acid β, β, β-trichloroethylester.

18. 7-[S(+)- α-Hydrazinophenylacetamido]-desacetoxycephalosporanic acid β, β, β-trichloroethylester.

19. A pharmaceutical composition comprising an anti-bacterially effective amount of a compound as defined in claim 1 and a pharmaceutically acceptable carrier.

* * * * *

UNITED STATES PATENT AND TRADEMARK OFFICE
CERTIFICATE OF CORRECTION

PATENT NO. : 3,998,950
DATED : December 21, 1976
INVENTOR(S) : Renato BROGGI et al.

It is certified that error appears in the above-identified patent and that said Letters Patent are hereby corrected as shown below:

Column 2, line 62, change "a" to --at--.
Column 3, line 6, change "$[\alpha]_D^{25°C}$ 32 + 125°" to --$[\alpha]_D^{25°C}$ = +125°--;
Column 3, line 30, change "chloric" to --chloride--;
Column 3, line 39, change "chlorie" to --chloride--.
Column 4, line 55, change "evapoated" to --evaporated--.
Column 6, line 39, change "$[\alpha]_D^{25°C}$ =+65° (C=a," to --$[\alpha]_D^{25°C}$ = +53.7°C (C = 1,--.

Signed and Sealed this

Fifth Day of April 1977

[SEAL]

Attest:

RUTH C. MASON
Attesting Officer

C. MARSHALL DANN
Commissioner of Patents and Trademarks